US011370749B2

(12) United States Patent
Favero et al.

(10) Patent No.: US 11,370,749 B2
(45) Date of Patent: Jun. 28, 2022

(54) METHOD FOR TREATING A SUSPENSION OF SOLID PARTICLES IN WATER USING A (CO)POLYMER OF A HYDRATED CRYSTALLINE FORM OF 2-ACRYLAMIDO-2-METHYLPROPANESULFONIC ACID

(71) Applicant: SPCM SA, Andrezieux Boutheon (FR)

(72) Inventors: Cédrick Favero, Andrezieux Boutheon (FR); Johann Kieffer, Andrezieux Boutheon (FR); Frédéric Daguerre, Andrezieux Boutheon (FR)

(73) Assignee: SPCM SA, Andrezieux Boutheon (FR)

( * ) Notice: Subject to any disclaimer, the term of this patent is extended or adjusted under 35 U.S.C. 154(b) by 272 days.

(21) Appl. No.: 16/494,587

(22) PCT Filed: Mar. 19, 2018

(86) PCT No.: PCT/FR2018/050660
§ 371 (c)(1),
(2) Date: Sep. 16, 2019

(87) PCT Pub. No.: WO2018/172683
PCT Pub. Date: Sep. 27, 2018

(65) Prior Publication Data
US 2020/0087186 A1    Mar. 19, 2020

(30) Foreign Application Priority Data

Mar. 20, 2017   (FR) .................... 1752288

(51) Int. Cl.
| | | |
|---|---|---|
| *C07C 309/15* | (2006.01) | |
| *C02F 1/56* | (2006.01) | |
| *C02F 11/147* | (2019.01) | |
| *C09K 8/588* | (2006.01) | |
| *C09K 8/80* | (2006.01) | |
| *E21B 43/16* | (2006.01) | |
| *E21B 43/26* | (2006.01) | |
| *C08F 20/58* | (2006.01) | |
| *C09K 8/68* | (2006.01) | |
| *C02F 103/10* | (2006.01) | |
| *C09K 8/88* | (2006.01) | |
| *C07C 309/21* | (2006.01) | |
| *C07C 303/02* | (2006.01) | |
| *C07C 303/44* | (2006.01) | |
| *C08F 20/56* | (2006.01) | |

(52) U.S. Cl.
CPC .............. *C07C 309/15* (2013.01); *C02F 1/56* (2013.01); *C02F 11/147* (2019.01); *C08F 20/58* (2013.01); *C09K 8/588* (2013.01); *C09K 8/68* (2013.01); *C09K 8/80* (2013.01); *E21B 43/16* (2013.01); *E21B 43/26* (2013.01); *C02F 2103/10* (2013.01); *C07B 2200/13* (2013.01); *C09K 2208/28* (2013.01)

(58) Field of Classification Search
USPC ...................................... 175/66, 206, 207
See application file for complete search history.

(56) References Cited

U.S. PATENT DOCUMENTS

| | | | |
|---|---|---|---|
| 4,347,140 | A | 8/1982 | Condolios et al. |
| 10,759,746 | B2 | 9/2020 | Favero et al. |
| 2004/0035800 | A1* | 2/2004 | Weir ............... C02F 1/56 210/723 |
| 2010/0274048 | A1 | 10/2010 | Wakayama |
| 2020/0048535 | A1 | 2/2020 | Favero et al. |
| 2020/0079992 | A1 | 3/2020 | Favero et al. |

FOREIGN PATENT DOCUMENTS

| | | |
|---|---|---|
| CA | 1273888 A | 9/1990 |
| CA | 2407869 A1 | 12/2001 |
| CA | 2515581 A1 | 7/2004 |
| CA | 2682542 A1 | 4/2010 |
| EP | 2203245 B1 | 7/2010 |
| WO | 96/05146 A1 | 2/1996 |
| WO | 2016/128638 A1 | 8/2016 |

OTHER PUBLICATIONS

International Search Report (and English translation) and Written Opinion of the International Searching Authority for International Application No. PCT/FR2018/050660 dated Jun. 1, 2018.
Favero et al., "Hydrated Crystalline Form of 2-Acrylamido-2-Methylpropane Sulfonic Acid," U.S. Appl. No. 16/926,159, filed Jul. 10, 2020, 58 pp.

\* cited by examiner

*Primary Examiner* — Clare M Perrin
(74) *Attorney, Agent, or Firm* — Heslin Rothenberg Farley & Mesiti P.C.

(57) ABSTRACT

The present invention relates to a method for the treatment of a suspension of solid particles in water using water-soluble (co)polymers made from the hydrated crystalline form of 2-acrylamido-2-methylpropane sulfonic acid or of at least one of the salts thereof. This method is particularly useful for treating residues resulting from the mining industry.

20 Claims, No Drawings

METHOD FOR TREATING A SUSPENSION OF SOLID PARTICLES IN WATER USING A (CO)POLYMER OF A HYDRATED CRYSTALLINE FORM OF 2-ACRYLAMIDO-2-METHYLPROPANESULFONIC ACID

CROSS REFERENCE TO RELATED APPLICATIONS

This application is a national stage filing under section 371 of International Application No. PCT/FR2018/050660 filed on Mar. 19, 2018, and published on Sep. 27, 2018 as WO 2018/172683, which claims priority to French Application No. 1752288, filed on Mar. 20, 2017. The entire contents of WO 2018/172683 are hereby incorporated herein by reference.

FIELD OF THE INVENTION

The present invention relates to a method for the treatment of a suspension of solid particles in water, such as mining industry residues, using water-soluble (co)polymers made from the hydrated crystalline form of 2-acrylamido-2-methylpropane sulfonic acid or of at least one of the salts thereof. The method comprises the step of placing said suspension in contact with water-soluble (co)polymers made from the hydrated crystalline form of 2-acrylamido-2-methylpropane sulfonic acid or at least one of the salts thereof.

The method according to the invention consists, inter alia, in adding said water-soluble (co)polymers to a thickener containing the suspension to be treated and/or during the transportation of said suspension to a depositing area for the dehydration and solidification thereof and/or in adding said water-soluble (co)polymers to said suspension and then performing a mechanical treatment, such as centrifugation, pressing or filtration.

DESCRIPTION OF THE PRIOR ART

Suspensions of solid particles in water comprise all types of sludge, residues and waste materials. Suspensions may result from the processing of ores. This may be for example sludge or industrial residues and all products from washing and mine waste resulting from mining operations, such as for example coal mines, diamond mines, phosphate mines, metal (aluminum, platinum, iron, gold, copper, silver, etc.) mines. Suspensions may also result from sludge or extraction residues derived from the processing of bituminous sand. These suspensions of solid particles comprise generally organic and/or mineral particles, such as for example clays, sediments, sand, metal oxides, oil, etc. mixed with water.

The term "suspension" is used hereinafter and refers to suspensions of solid particles as described above.

The treatment of these residues and other waste materials has become a technical, environmental, and public order problem. The use of synthetic or natural polymers, such as coagulants and flocculants, to separate the solids from the liquid is a current practice.

For a long time, and even now, mineral sludge produced by physical or chemical treatment of ores has been stored in the open in lagoons, ponds, tailings dams or backfills in semi-liquid form. These large volumes of stored sludge therefore create a real hazard, in particular if the embankments fail.

Since the traditional storage solutions are clearly hazardous, increasing numbers of national regulations have been published, prohibiting the abandonment of these areas. The regulations also oblige restoration of these sites, namely the treatment and consolidation of the land.

The improvement in chemical and mechanical treatments of residues or sludge is consequently an important challenge.

Various attempts have been carried out over recent decades to increase the rate of sedimentation of the residues in order to efficiently recycle the water and to reduce the volume of residue. The main physical treatments comprise centrifugation, filtration, electrophoresis, and electrocoagulation.

Furthermore, chemical processes have emerged. They comprise a method involving the addition of chemical products, such as sodium silicate, organic flocculants, inorganic coagulants, oxidizing and reducing agents, and more recently carbon dioxide.

In 1979-1980, Alsthom Atlantique and SNF (U.S. Pat. No. 4,347,140) developed a multiple-step flocculation system (superflocculation) specifically designed to treat the clay settling lagoons produced as a result of phosphate production in Florida.

Suspension treatment has been studied continuously: in 1986 in accordance with the method described in CA 1,273,888, then in 1994 in WO 96/05146, in 2000 in CA 2,407,869 and in 2004 in CA 1,515,581.

In document CA 2,682,542, the method involves the addition of polymers modified by copolymerization and/or branching. Polymers with hydrophobic groups, which have also been studied, have shown an improvement in the treatment of suspensions.

Despite major advances in recent years, there is still a need to develop (co)polymers which enable the rate and quantity of water released from suspensions to be increased. An improvement of the physical characteristics of the dehydrated sludge produced is also sought.

DISCLOSURE OF THE INVENTION

The present invention meets the aforementioned requirements by virtue of a method for the treatment of a suspension of solid particles in water using at least one water-soluble (co)polymer made from the hydrated crystalline form of 2-acrylamido-2-methylpropane sulfonic acid or of at least one of the salts thereof.

The invention relates to a method for the treatment of a suspension of solid particles in water, comprising the placing of said suspension in contact with at least one water-soluble (co)polymer made from the hydrated crystalline form of 2-acrylamido-2-methylpropane sulfonic acid or of at least one of the salts thereof.

Broadly speaking, unless otherwise indicated, "2-acrylamido-2-methylpropane sulfonic acid in hydrated crystalline form" denotes the acid form and/or the salified form. The same is the case for the anionic monomers that may denote the acid and/or salified forms like, for example, for acrylic acid.

According to a preferred embodiment of the invention, the (co)polymer of the invention is made from the saline form of 2-acrylamido-2-methylpropane sulfonic acid in hydrated crystalline form. The 2-acrylamido-2-methylpropane sulfonic acid is therefore preferably partially or totally salified before polymerization. The acid form of a monomer can be salified before and/or during and/or after the (co)polymerization of the monomer or monomers.

In a very surprising way, the use of at least one water-soluble (co)polymer made from the hydrated crystalline form of 2-acrylamido-2-methylpropane sulfonic acid or from at least one of the salts thereof allows for the efficient treatment of suspensions of solids. It is the use of the hydrated crystalline form of the 2-acrylamido-2-methylpropane sulfonic acid in the preparation of the water-soluble (co)polymer, that conveys to said (co)polymer particular properties, thereby making it possible to improve the treatment of solid particles in suspensions.

By definition, a water-soluble (co)polymer is a (co)polymer that produces an aqueous solution when it is dissolved with stirring at 25° C. and with a concentration of 50 g·L$^{-1}$ in water.

The hydrated crystalline form of 2-acrylamido-2-methylpropane sulfonic acid having a 2-theta powder X-ray diffraction diagram comprised of peaks at 10.58°, 11.2°, 12.65°, 13.66°, 16.28°, 18.45°, 20°, 20.4°, 22.5°, 25.5°, 25.88°, 26.47°, 28.52°, 30.28°, 30.8°, 34.09°, 38.19°, 40.69°, 41.82°, 43.74°, 46.04° degrees. The uncertainty in these peaks is generally of the order of 0.1°.

X-ray crystallography, radiocrystallography or X-ray diffractometry is an analytical technique for studying the structure of the crystalline material on the atomic scale. It uses the physical phenomenon of X-ray diffraction. A diffractometer having a copper source may be used.

A powder formed from a given crystalline phase will always produce diffraction peaks in the same directions. So this diffraction diagram forms a real signature of the crystalline phase. It is therefore possible to determine the nature of each crystalline phase in a mixture or a pure product.

This signature is specific to each crystalline organic or inorganic compound, and presents in the form of a list of peaks with positions at the 2θ angle (2-theta).

This technique is used to characterize the material, particularly the different crystalline forms that may exist for a given chemical molecule.

The hydrated crystalline form of 2-acrylamido-2-methylpropane sulfonic acid having a Fourier transform infrared spectrum comprising peaks at 3280 cm$^{-1}$, 3126 cm$^{-1}$, 1657 cm$^{-1}$, 1595 cm$^{-1}$, 1453 cm$^{-1}$, 1395 cm$^{-1}$, 1307 cm$^{-1}$, 1205 cm$^{-1}$, 1164 cm$^{-1}$, 1113 cm$^{-1}$, 1041 cm$^{-1}$, 968 cm$^{-1}$, 885 cm$^{-1}$, 815 cm$^{-1}$, 794 cm$^{-1}$. The uncertainty in these peaks is generally of the order of 8 cm$^{-1}$. Advantageously, this is the solid spectrum obtained conventionally in a salt such as KBr.

Fourier transform infrared spectroscopy is the analysis of vibrations emitted, absorbed or diffused by the molecules. This technique is sensitive to close interactions (influence of the lattice unit on the bonds). In the majority of cases, the Fourier transform infrared spectra for different crystalline systems differ significantly. So the Fourier transform infrared spectrum reflects details about the crystalline structure of an organic compound.

Generally, and unless otherwise indicated, the X-ray diffraction diagram and the infrared spectrum are obtained at 20° C. and atmospheric pressure of 1 atmosphere (101,325 Pa).

The hydrated crystalline form of 2-acrylamido-2-methylpropane sulfonic acid having minimum ignition energy greater than 400 mJ, preferably greater than 500 mJ (1 mJ=10$^{-3}$ joule).

The minimum ignition energy represents the minimum energy that must be provided to a compound to cause ignition. The energy may be electric or thermal. The minimum ignition energy is an essential piece of data for taking into account the risk of explosion during product handling (transfer, storage, reaction, shaping, etc.).

The minimum ignition energy depends on the powder's properties (composition) and its macromolecular structure (particle size, crystalline form, specific surface area).

For solids, this energy is the minimum energy of an electrical spark that can ignite a cloud of dust. The higher the minimum ignition energy, the lower the risk the solid presents during use, handling, storage.

Minimum Ignition Energy was Measured According to Standard NF EN 13821.

The hydrated crystalline form of 2-acrylamido-2-methylpropane sulfonic acid presenting 4 thermal phenomena with the differential scanning calorimetry technique, at 70° C., 100° C., 150° C. and 190° C. The relative uncertainty when observing these phenomena is generally of the order of 10° C., advantageously 5° C. or less.

The thermal phenomena are measured by differential scanning calorimetry (DSC). This technique measures the heat variation associated with thermal denaturation of the compound when it is heated at a constant rate, for example with a heating ramp of 10° C./minute.

It is generally recognized that the thermal phenomenon that occurs at 190° C. (+/−10° C.) is related to the melting point of 2-acrylamido-2-methylpropane sulfonic acid.

According to the invention it was found in a surprising manner that the use of a (co)polymer made from the hydrated crystalline form of 2-acrylamido-2-methylpropane sulfonic acid improves the performance of the treatment of suspensions in regard to:

the increase in the concentration of sludge at the outlet of a thickener, or the dehydration step and the drying and solidification steps of the suspensions when discharged onto the ground, or the mechanical treatment of the treated suspensions.

A further aspect of the invention is a method for the flocculation of a suspension of solid particles in water, comprising the placing of said suspension in contact with at least one water-soluble (co)polymer prepared from the hydrated crystalline form of 2-acrylamido-2-methylpropane sulfonic acid or of at least one of the salts thereof.

According to a specific embodiment of the invention, the water-soluble (co)polymer is at the least made from 2-acrylamido-2-methylpropane sulfonic acid; 50% to 100% of 2-acrylamido-2-methylpropane sulfonic is advantageously in hydrated crystalline form, more advantageously 70 to 100%, and even more advantageously 100%.

Unless otherwise indicated (the quantity of branching/crosslinking agent and the quantity of solid particles in the suspension to be treated), the percentages are molar percentages.

The water-soluble (co)polymer is advantageously obtained from between 0.1 and 100 mol % of 2-acrylamido-2-methylpropane sulfonic acid, preferably between 2 and 60 mol % of 2-acrylamido-2-methylpropane sulfonic acid, even more preferably between 3 and 25 mol % of 2-acrylamido-2-methylpropane sulfonic acid; 50% to 100% of 2-acrylamido-2-methylpropane sulfonic acid being advantageously in the hydrated crystalline form, more advantageously 70 to 100%, and even more advantageously 100%.

According to a preferred embodiment of the invention, the (co)polymer of the invention is made from the saline form of 2-acrylamido-2-methylpropane sulfonic acid in hydrated crystalline form. The 2-acrylamido-2-methylpropane sulfonic acid is therefore preferably partially or totally salified before polymerization. Preferentially it is completely salified.

The salt form is advantageously obtained from a compound chosen from among an alkali or alkaline earth metal hydroxide, an alkali or alkaline metal earth oxide, ammonia, an amine having the following formula $NR_1R_2R_3$ ($R_1$, $R_2$ and $R_3$ being advantageously hydrocarbon groups, in particular alkyl groups) or an alkali or alkaline earth metal carbonate. A preferred alkaline metal is sodium.

The water-soluble (co)polymer is, preferentially, made from the hydrated crystalline form of 2-acrylamido-2-methylpropane sulfonic acid or of at least one of the salts thereof, and from at least one nonionic monomer, and/or at least one anionic monomer, and/or at least one cationic monomer and/or at least one zwitterionic monomer.

The nonionic monomer or monomers that can be used in the scope of the invention can be chosen, in particular, in the group comprising water-soluble vinyl monomers. Preferred monomers belonging to this class are, for example, acrylamide, methacrylamide, N-isopropylacrylamide, N,N-dimethylacrylamide, N,N-diethylacrylamide and N-methylolacrylamide. The following may also be used: N-vinylformamide, N-vinyl acetamide, N-vinylpyridine and N-vinylpyrrolidone, N-vinyl imidazole, N-vinyl succinimide, acryloyl morpholine (ACMO), acryloyl chloride, glycidyl methacrylate, glyceryl methacrylate, diacetone acrylamide and isoprenol. A preferred nonionic monomer is acrylamide.

According to a particular embodiment, the water-soluble (co)polymer is advantageously obtained from between 1 and 99.9 mol % of nonionic monomer(s), preferably between 40 and 95 mol % and more preferably between 45 and 90 mol %, in relation to the total number of monomers. In this case, the (co)polymer is advantageously obtained from between 0.1 and 99 mol % of 2-acrylamido-2-methylpropane sulfonic acid, and more preferably between 10 and 55 mol %; 50% to 100% of the 2-acrylamido-2-methylpropane sulfonic acid being advantageously in the hydrated crystalline form, more advantageously 70 to 100%, and even more advantageously 100%.

The anionic monomer(s) that may be used within the scope of the invention may be selected from a wide group. These monomers may have acrylic, vinyl, maleic, fumaric, malonic, itaconic or allylic functional groups and contain a carboxylate, phosphonate, phosphate, sulfate, sulfonate group or another anionic group. The anionic monomer may be in acid form or in the form of an alkaline earth metal salt, an alkali metal salt or an ammonium salt. Examples of suitable monomers include acrylic acid; methacrylic acid; itaconic acid; crotonic acid, maleic acid; fumaric acid; acrylamido undecanoic acid; 3-acrylamido 3-methylbutanoic acid; maleic anhydride; monomers of the strong acid type having for example a function of the sulfonic acid or phosphonic acid type such as vinylsulfonic acid, vinylphosphonic acid, allylsulfonic acid, methallylsulfonic acid, 2-methylidenepropane-1,3-disulfonic acid, 2-sulfoethylmethacrylate, sulfopropylmethacrylate, sulfopropylacrylate, allylphosphonic acid, styrene sulfonic acid, 2-acrylamido-2-methyl propane disulfonic acid; and the water-soluble salts of these monomers such as the alkali metal, alkaline earth metal, or ammonium salts thereof. In this list, the strong acid monomers mentioned having a sulfonic acid function do not include the hydrated crystalline form of 2-acrylamido-2-methylpropane sulfonic acid.

According to a particular embodiment, the (co)copolymer is advantageously made from between 0.1 and 100 mol % of anionic monomer(s), preferably between 1 and 99 mol %, and more preferably between 5 and 70% and even more preferably between 10 and 50 mol %, in relation to the total number of monomers. In this case, these percentages also include the hydrated crystalline form of 2-acrylamido-2-methylpropane sulfonic acid according to the invention.

The cationic monomer(s) that can be used within the scope of the invention may be chosen from among monomers derived from units of the acrylamide, acrylic, vinyl, allyl or maleic type, where these monomers have a quaternary phosphonium or ammonium function. Mention may be made, in a particular and in a non-limiting way, of quaternized dimethylaminoethyl acrylate, quaternized dimethylaminoethyl acrylate, dimethyldiallylammonium chloride (DADMAC), acrylamido propyltrimethyl ammonium chloride (APTAC) and methacrylamido propyltrimethyl ammonium chloride (MAPTAC). The quaternization agent may be chosen from alkyl chlorides, dialkyl sulfates or alkyl halides. Preferably, the quaternization agent is chosen from methyl chloride or diethyl sulfate.

The acidified salts are obtained by means known to a person skilled in the art, and notably by protonation. The quaternized salts are also obtained by means known to a person skilled in the art, notably by reaction with benzyl chloride, methyl chloride (MeCl), aryl chlorides, alkyl chlorides, or dialkylsulfates such as dimethylsulfate.

According to a preferred embodiment, the cationic monomer is selected from diallyldialkyl ammonium salts such as diallyl dimethyl ammonium chloride (DADMAC), acidified or quaternized salts of dialkyl-aminoalkylacrylamides or methacrylamides, such as for example methacrylamidopropyl trimethyl ammonium chloride (MAPTAC) or acrylamido-propyl trimethyl ammonium chloride (APTAC).

When a monomer having a cationic nature is used for the preparation of the water-soluble (co)polymer, the quantity thereof lies advantageously within the range between 0.01 and 20 mol % in relation to the total quantity of monomers, more preferably between 0.2 and 6 mol %.

The zwitterionic monomer could be an acrylamide, acrylic, vinyl, allyl or maleic derivative having an amine or quaternary ammonium function and an acid function like a carboxylic (or carboxylate), sulfonic (or sulfonate) or phosphoric (or phosphonate) acid. Mention may be made, specifically and in a non-limiting manner, of dimethylaminoethyl acrylate derivatives, such as 2-((2-(acryloyloxy)ethyl) dimethylammonio) ethane-1-sulfonate, 3-((2-(acryloyloxy) ethyl) dimethylammonio) propane-1-sulfonate, 4-((2-(acryloyloxy)ethyl) dimethylammonio) butane-1-sulfonate, [2-(acryloyloxy)ethyl)] (dimethylammonio)acetate, dimethylaminoethyl methacrylate derivatives such as 2-((2-(methacryloyloxy)ethyl) dimethylammonio) ethane-1-sulfonate, 3-((2-(methacryloyloxy) ethyl) dimethylammonio) propane-1-sulfonate, 4-((2-(methacryloyloxy) ethyl) dimethylammonio) butane-1-sulfonate, [2-(methacryloyloxy)ethyl)] (dimethylammonio)acetate, dimethylamino propylacrylamide derivatives such as 2-((3-acrylamidopropyl) dimethylammonio) ethane-1-sulfonate, 3-((3-acrylamidopropyl) dimethylammonio) propane-1-sulfonate, 4-((3-acrylamidopropyl) dimethylammonio) butane-1-sulfonate, [3-(acryloyloxy) propyl)] (dimethylammonio) acetate, dimethylamino propyl methylacrylamide derivatives such as 2-((3-methacrylamidopropyl) dimethylammonio) ethane-1-sulfonate, 3-((3-methacrylamidopropyl) dimethylammonio) propane-1-sulfonate, 4-((3-methacrylamidopropyl) dimethylammonio) butane-1-sulfonate and [3-(methacryloyloxy) propyl)] (dimethylammonio) acetate.

When a monomer having a zwitterionic nature is used for the preparation of the water-soluble (co)polymer, the quantity thereof lies advantageously within the range between 0.01 and 20 mol % in relation to the total quantity of monomers, more preferably between 0.1 and 10 mol %.

Monomers with a hydrophobic nature may also be used in the preparation of the water-soluble (co)polymer used in the method of the invention. They are preferably selected from the group consisting of (meth)acrylic acid esters having an alkyl, arylalkyl, propoxylated, ethoxylated, or propoxylated and ethoxylated chain; (meth)acrylamide derivatives having an alkyl, arylalkyl, propoxylated, ethoxylated, ethoxylated and propoxylated, or dialkyl chain; alkyl aryl sulfonates.

When a monomer having a hydrophobic nature is used for the preparation of the water-soluble (co)polymer, the quantity thereof lies advantageously within the range between 0.001 and 3 mol % in relation to the total quantity of monomers.

The water-soluble (co)polymer is preferably an anionic (co)polymer based on acrylamide and 2-acrylamido-2-methylpropane sulfonic acid; 50% to 100% of the 2-acrylamido-2-methylpropane sulfonic acid being in the hydrated crystalline form and/or the salts thereof. This is preferably a terpolymer of acrylamide, of acrylic acid and of 2-acrylamido-2-methylpropane sulfonic acid; 50% to 100% of the 2-acrylamido-2-methylpropane sulfonic acid being in the hydrated crystalline form and/or the salts thereof. In both cases, the (co)polymer can be partially or totally post hydrolyzed, the anionic monomers that can be in the acid or salified form.

In a preferred manner, the water-soluble (co)polymer contains only monomeric anionic and nonionic units. In other words, it is preferably obtained from at least one anionic monomer and at least one nonionic monomer.

According to the invention, the water-soluble (co)polymer may have a linear, branched, star-shaped, comb-shaped, dendritic or block structure. These structures may be obtained by the selection of the initiator, transfer agent, polymerization technique, such as controlled radical polymerization known as RAFT (reversible-addition fragmentation chain transfer), NMP (nitroxide-mediated polymerization) or ATRP (atom-transfer radical polymerization), by the incorporation of structural monomers, or by the concentration, etc.

According to the invention, the water-soluble (co)polymer is advantageously linear or structured. Structured (co)polymer denotes a non-linear (co)polymer that has side chains so as to obtain, when this (co)polymer is dissolved in water, a high state of tangling leading to viscosities with very high low gradients. The water-soluble (co)polymer according to the invention is not generally crosslinked.

The water-soluble (co)polymer may in addition be structured:
  by at least one structure agent, which can be chosen from the group comprising unsaturated polyethylene monomers (having at least two unsaturated functions), such as for example vinyl, allyl, acrylic and epoxy functions and for example mention may be made of methylene-bis-acrylamide (MBA), triallyamine, tetraallylammonium chloride, or 1,2-dihydroxyethylene bis-(N-acrylamide), and/or
  by macroinitiators such as polyperoxides, polyazoics and poly transfer agents such as polymercaptan (co)polymers, and polyols, and/or
  by functionalized polysaccharides The quantity of branching/crosslinking agent in the monomer mixture is advantageously less than 4% by weight relative to the monomer content, more advantageously less than 1% and even more advantageously less than 0.5%. According to a specific embodiment, it may at least equal to 0.00001% by weight in relation to the monomer content.

Monomers with a fluorescent function may also be used in the scope of the invention. A monomer with a fluorescent function may be detected by any appropriate method, for example by fluorimetry with a fixed wavelength fluorimeter. Generally, the monomer having a fluorescent function is detected at the excitation and emission maxima, which can be determined using a scanning fluorimeter.

Those monomers having a fluorescent function are chosen from, for example, monomers comprising sodium sulfonate styrene and sulfonic styrene.

Generally, the (co)polymer does not require the development of any particular polymerization method. Indeed, it may be obtained according to polymerization techniques known by a person skilled in the art. It may notably be solution polymerization, gel polymerization, precipitation polymerization, emulsion polymerization (aqueous or inverse), suspension polymerization, reactive extrusion polymerization, water-in-water polymerization, or micellar polymerization.

Polymerization is generally a free-radical polymerization preferably by inverse emulsion polymerization or gel polymerization. By free-radical polymerization, we include free-radical polymerization by means of UV initiators, azo initiators, redox or thermal initiators as well as controlled radical polymerization (CRP) or matrix polymerization techniques.

According to a specific embodiment of the invention, the (co)polymer may be post-hydrolyzed. Post-hydrolysis is the reaction of the (co)polymer after polymerization. This step consists in reacting the hydrolyzable functional groups on the advantageously nonionic monomers, more advantageously amide or ester functions, with a hydrolysis agent. This hydrolysis agent may be an enzyme, an ion exchange resin, or an alkali metal. Preferably, the hydrolysis agent is a base. During this (co)polymer post-hydrolysis step, the number of carboxylic acid functions increases. Indeed the reaction between the base and the amide or ester functions in the (co)polymer produces carboxylate groups.

According to the invention, the (co)polymer may be in the form of a liquid, gel or solid when the preparation thereof includes a drying step such as spray drying, tumble drying, drying by electromagnetic radiation such as microwave or fluidized bed drying.

According to a specific embodiment, the water-soluble (co)polymer may comprise at least one LCST group.

According to the general knowledge of a person skilled in the art, LCST groups correspond to groups whose water solubility for a determined concentration is modified beyond a certain temperature and as a function of the salinity. This is a group having a heating transition temperature defining its lack of affinity with the solvent medium. The lack of affinity with the solvent results in opacification or loss of transparency, which may be due to precipitation, aggregation, gelification, or viscosification of the medium. The minimum transition temperature is known as "LCST" (Lower Critical Solution Temperature). For each concentration of the LCST group, a heating transition temperature is observed. It is greater than the LCST, which is the minimum point in the curve. Below this temperature, the polymer is soluble in water; above this temperature, the polymer loses its solubility in water.

According to a specific embodiment, the water-soluble (co)polymer may comprise at least one UCST group.

According to the general knowledge of a person skilled in the art, UCST groups correspond to groups whose water solubility for a determined concentration is modified beyond a certain temperature and as function of the salinity. This is a group having a cooling transition temperature defining its lack of affinity with the solvent medium. The lack of affinity with the solvent results in opacification or loss of transparency, which may be due to precipitation, aggregation, gelification, or viscosification of the medium. The maximum transition temperature is known as "UCST" (Upper Critical Solution Temperature). For each concentration of the UCST group, a cooling transition temperature is observed. It is lower than the UCST, which is the maximum point in the curve. Above this temperature, the (co)polymer is soluble in water; below this temperature, the (co)polymer loses its water solubility.

According to the invention, the water-soluble (co)polymer has an advantageously high molecular weight. "High molecular weight" denotes molecular weights of at least 0.5 million g/mol, preferably between 0.5 and 40 million g/mol, more preferably between 5 and 30 million g/mol. Molecular weight is understood as average molecular weight by weight. The water-soluble (co)polymer can also have a molecular weight between 5,000 and 100,000 g/mol or between 100,000 and 500,000 g/mol.

The molecular weight is determined by the intrinsic viscosity of the (co)polymer. The intrinsic viscosity may be measured by methods known to the person skilled in the art and may be calculated from lower viscosity values for different (co)polymer concentrations by a graphic method consisting in recording the lower viscosity values (y-axis) over the concentration (x-axis) and extrapolating the curve to zero concentration. The intrinsic viscosity value is recorded on the y-axis or using the least squares method. The molecular weight may then be determined by the Mark-Houwink equation:

$$[\eta]=KM^\alpha$$

[η] represents the intrinsic viscosity of the (co)polymer determined by the method for measuring viscosity in solution.

K represents an empirical constant.

M represents the molecular weight of the (co)polymer.

α represents the Mark-Houwink coefficient.

K and α depend on the specific (co)polymer-solvent system.

As previously mentioned, the invention relates to a method for the treatment of a suspension of solid particles in water, comprising the placing of said suspension in contact with at least one water-soluble (co)polymer, said (co)polymer being made from the hydrated crystalline form of 2-acrylamido-2-methylpropane sulfonic acid or of at least one of the salts thereof. It involves mixing said suspension with the water-soluble (co)polymer of the invention.

Such a treatment may be carried out in a thickener, which is a holding area, generally in the form of a section of tube several meters in diameter with a conical bottom into which particles can settle. According to a specific embodiment, the aqueous suspension is transported through a pipe (conduit) to a thickener and the water-soluble (co)polymer according to the invention is added within said pipe.

According to another specific embodiment, the water-soluble (co)polymer according to the invention is added to the thickener which already contains the suspension to be treated. In a typical mineral treatment operation, the suspensions are often concentrated in a thickener. This results in a sludge of higher density being obtained which leaves by the base of the thickener, and an aqueous fluid released from the treated suspension (known as liquor) which leaves by the overflow at the top of the thickener. The addition of the water-soluble (co)polymer according to the invention increases the concentration of the sludge and increases the clarity of the solution.

According to another specific embodiment, the water-soluble (co)polymer according to the invention is added to the suspension of particles during the transport of said suspension to a depositing area. Preferably, the water-soluble (co)polymer according to the invention is added within the pipe which transports said suspension to a depositing area. It is over this depositing area that the treated suspension is spread with a view to the dehydration and solidification thereof. The depositing areas may be open, such as for example a non-bounded area of ground, or closed, such as for example a lagoon, a unit.

One example of these treatments during the transportation of the suspension is the spreading of the suspension, treated with the water-soluble (co)polymer according to the invention, over the ground with a view to the dehydration and solidification thereof, then the spreading of a second layer of treated suspension over the first solidified layer. Another example is the continuous spreading of the suspension treated with the water-soluble (co)polymer according to the invention such that the treated suspension continuously falls onto the suspension previously discharged into the depositing area, thus forming a heap of treated material from which the water is extracted.

According to another specific embodiment, the water-soluble (co)polymer according to the invention is added to the suspension, and a mechanical treatment is then performed, such as centrifugation, pressing, or filtration.

The water-soluble (co)polymer according to the invention may be added simultaneously in the various stages of the treatment of the suspension, i.e., for example, into the pipe (conduit) transporting the suspension to a thickener and into the sludge leaving the thickener which will then be taken either to a depositing area, or to mechanical treatment apparatus.

The water-soluble (co)polymer according to the invention can be added to the aqueous suspension to be treated, in the form of a liquid or a solid. It can be added in the form of an emulsion (water in oil), of a multiphase aqueous, oily or powder particulate suspension. The (co)polymer is preferably added in the form of an aqueous solution made from a concentrated form of the polymer as a powder, a water-in-oil emulsion or a multiphase aqueous or oily particulate suspension.

According to a specific embodiment of the invention, the multiphase aqueous particulate suspension preferably comprises:
  i. 15 to 60% by mass of at least a water-soluble (co)polymer according to the invention in the form of solid particles with an average size of between 5 and 500 µm;
  ii. 15 to 45% by of at least one alkali metal salt and/or of at least one salt of an alkaline earth metal;
  iii. at least one viscosifying agent other than the water-soluble polymer;
  iv. at least 10% by mass of water; and
     said suspension having a Brookfield viscosity between 500 and 20,000 cps at a temperature of 20° C., and said suspension having a density between 1.1 and 2 kg·L$^{-1}$.

According to a specific embodiment of the invention, the multiphase oily particulate suspension preferably comprises:
  i—15 to 60% by mass of at least a water-soluble (co) polymer according to the invention in the form of solid particles with an average size of between 5 and 500 µm;

ii—at least one viscosifying agent other than the water-soluble polymer;
iii—at least 10% by mass of oil; and
said suspension having a Brookfield viscosity between 500 and 20,000 cps at a temperature of 20° C., and said suspension having a density between 0.6 and 1.4 kg·L$^{-1}$.

The Brookfield viscosity is measured using a Brookfield device mounted onto an LV spindle, where the spindle can, for example, turn at a speed of 30 rotations per minute, the measurement being advantageously performed at 20° C. The density is measured at 20° C., at a pressure of 1 ATM, i.e. 101,325 Pa.

When the water-soluble (co)polymer according to the invention is in the form of a solid, it may be partially or fully dissolved in water using a (co)polymer preparation unit such as the Polymer Slicing Unit (PSU) disclosed in document EP 2,203,245.

According to another specific embodiment, the water-soluble (co)polymer according to the invention is added to the suspension in combination with at least another synthetic or natural polymer. These polymers can be separately or simultaneously added (before or after the addition of the water-soluble (co)polymer according to the invention). The other polymer can be water-soluble or water-swellable. It may be a dispersant, coagulant or a flocculant.

According to another specific embodiment, the water-soluble (co)polymer according to the invention is added to the suspension in combination with a salt such as salts of calcium and/or magnesium. The water-soluble (co)polymer according to the invention and the salt can be added simultaneously or separately. The salts may be inorganic or organic. Suitable salts include calcium chloride, calcium acetate, calcium sulfate, calcium nitrate, calcium hydroxide, calcium carbonate, magnesium chloride, magnesium acetate, magnesium sulfate, magnesium nitrate, magnesium hydroxide, magnesium carbonate, calcium formate, calcium gluconate, calcium propionate, tricalcium phosphate and calcium succinate.

According to the invention, the quantity (proportion) of water-soluble (co)polymer added is between 50 and 5,000 g per metric ton of dry solids of the suspension, preferably between 250 and 2,000 g/t and more preferably between 500 and 1,500 g/t, depending upon the nature and composition of the suspensions to be treated.

According to the invention, the method using the (co) polymer described in the invention enables a suspension of solid particles and more particularly mineral particles to be effectively treated.

Suspensions of solid particles in water comprise all types of sludge, residues and waste materials. The suspensions especially result from ore extraction and are in the form of suspensions of mineral particles. They may, for example, correspond to sludge or industrial residues and all products from washing and mine waste resulting from mining operations, such as for example coal mines, diamond mines, phosphate mines, metal (aluminum, platinum, iron, gold, copper, silver, etc.) mines. Suspensions may also result from the extraction of bituminous sand, for example sludge or extraction residues derived from the treatment of bituminous sand. These suspensions generally comprise organic and/or mineral particles, such as for example clays, sediments, sand, metal oxides, oil, etc. mixed with water.

Generally, suspensions of solid particles are concentrated and contain between 5% and 60% by weight of solids, preferably between 20% and 50% by weight of solids, in relation to the total weight of said suspensions.

The method according to the invention can also useful for the treatment of residues from the extraction of bituminous sand: residues known as "fines" or "fine tailings", i.e., containing a large quantity of clays, and for the treatment of fine residues known as Mature Fine Tailings (MFT), i.e., these same residues after a few years of sedimentation, and containing an even greater quantity of clays. The method according to the invention may also be used to treat residues known as "fresh", i.e., coming directly from the operation of separating the bitumen and the soil from which it is extracted.

The following examples are provided by way of illustration only of the object of the invention, without limiting it in any way whatsoever.

EXAMPLES

Water-soluble polymers of different monomeric compositions are obtained by means of reactions in a 1.5 L reactor fitted with a mechanical agitator a thermometer and a nitrogen intake. The monomers are introduced into the reactor in the presence of distilled water. In order to exactly neutralize 100% of the acid monomers (ATBS) an appropriate quantity of caustic soda is added. The total concentration of the monomers in the reaction mixture is 25% by weight.

Two types of ATBS (2-acrylamido-2-methylpropane) powder are used, one in hydrated crystalline form according to the invention; the other is not in hydrated crystalline form, but rather in un-hydrated crystallized needle form.

The mixture thus obtained is then homogenized, then cooled and degassed using a stream of nitrogen. Polymerization is then initiated using a redox sodium hypophosphite and tert-butyl hydroperoxide system. The resulting gel, obtained after polymerization, is then ground and dried in a drying oven so as to obtain a powder.

The various polymers prepared are all water-soluble polymers with high molecular weights of between 10 and 12 million g/mol.

Polymer A (counter-example) is a copolymer of acrylamide (70 mol %) and 2-acrylamido-2-methylpropane sulfonic acid in hydrated non-crystalline form (30 mol %).

Polymer B (example according to the invention) is a copolymer of acrylamide (70 mol %) and 2-acrylamido-2-methylpropane sulfonic acid in hydrated crystalline form according to the invention (30 mol %).

Polymers A and B are dissolved in tap water in order to obtain aqueous solutions having a concentration of 0.4% by weight of polymer in relation to the total weight of the solution. The two solutions are mechanically stirred at 500 rpm until the polymers are completely dissolved and clear and homogeneous solutions are obtained.

A series of flocculation tests is performed on mine effluent from a carbon mine having a solids content of 19.6% by weight.

A quantity of each solution, corresponding to a polymer proportion of 280 g of polymer per ton of dry matter of the mining effluent is added to 200 g of mining effluent, complete mixing is then manually performed until flocculation and optimal water release are observed.

The result is expressed by virtue of the NWR (Net Water Release) which corresponds to the total quantity of water collected 1 hour after the flocculation test minus the quantity of water unduly added during the incorporation of the aqueous polymer solution into the suspension. The same NWR is calculated after 24 hours, this makes it possible to obtain a good overview of the maximum water release.

The NWR with polymer A is 68 mL versus 84 mL with polymer B. The NWR after 24 hours with polymer A is 72 mL versus 89 mL with polymer B. The water released during flocculation with polymer B is clearer than that released during flocculation with polymer A.

The results of this experiment clearly demonstrate that the use of 2-acrylamido-2-methylpropane sulfonic acid in hydrated crystalline form according to the invention makes it possible to obtain a more effective polymer for the flocculation of mining effluent from a coal mine.

Another series of tests is performed on red mud from a Bayer process, having a solids content of 24.5% by weight.

Polymer C (counter-example) is a copolymer of acrylamide (35 mol %) and 2-acrylamido-2-methylpropane sulfonic acid in hydrated non-crystalline form (65 mol %).

Polymer D (example according to the invention) is a copolymer of acrylamide (35 mol %) and 2-acrylamido-2-methylpropane sulfonic acid in hydrated crystalline form according to the invention (65 mol %).

The same test protocol that was used for the effluent from a coal mine is applied, with the difference that the quantity of polymer added here is 740 g of polymer per metric ton of dry solids of the red mud.

The NWR with polymer C is 42 mL versus 53 mL with polymer D. The NWR after 24 hours with polymer C is 45 mL versus 59 mL with polymer D. The water released during flocculation with polymer D is clearer than that released during flocculation with polymer C.

The results of this experiment clearly demonstrate that the use of 2-acrylamido-2-methylpropane sulfonic acid in hydrated crystalline form according to the invention makes it possible to obtain a more effective polymer for the flocculation of red mud from a Bayer process.

The invention claimed is:

1. A method for the treatment of a suspension of solid particles in water, comprising placing said suspension in contact with at least one water-soluble (co)polymer made from 2-acrylamido-2-methylpropane sulfonic acid or of at least one of the salts thereof,
   the 2-acrylamido-2-methylpropane sulfonic acid being a hydrated crystalline form of 2-acrylamido-2-methylpropane sulfonic acid having a 2-theta powder X-ray diffraction diagram comprising peaks at 10.58°, 11.2°, 12.65°, 13.66°, 16.28°, 18.45°, 20°, 20.4°, 22.5°, 25.5°, 25.88°, 26.47°, 28.52°, 30.28°, 30.8°, 34.09°, 38.19°, 40.69°, 41.82°, 43.74°, and 46.04°, all peak values being +/−0.1°.

2. The method according to claim 1, wherein the water-soluble (co)polymer is at the least made from 2-acrylamido-2-methylpropane sulfonic acid, 50% to 100% of the 2-acrylamido-2-methylpropane sulfonic acid being in hydrated crystalline form.

3. The method according to claim 2, wherein the water-soluble (co)polymer is made from the hydrated crystalline form of 2-acrylamido-2-methylpropane sulfonic acid or of at least one of the salts thereof, and from at least one nonionic monomer, and/or at least one anionic monomer.

4. The method according to claim 2, wherein the 2-acrylamido-2-methylpropane sulfonic acid in hydrated crystalline form is partially or totally salified before polymerization.

5. The method according to claim 4, wherein the water-soluble (co)polymer is made from the hydrated crystalline form of 2-acrylamido-2-methylpropane sulfonic acid or of at least one of the salts thereof, and from at least one nonionic monomer, and/or at least one anionic monomer.

6. The method according to claim 5, wherein the water-soluble (co)polymer is made from at least one nonionic monomer and/or at least one anionic monomer, and wherein:
   the at least one nonionic monomer is chosen from the group consisting of acrylamide, methacrylamide, N-isopropylacrylamide, N,N-dimethylacrylamide, N,N-diethylacrylamide and N-methylolacrylamide, N-vinylformamide, N-vinyl acetamide, N-vinylpyridine, N-vinylpyrrolidone, N-vinyl imidazole, N-vinyl succinimide, acryloyl morpholine (ACMO), acryloyl chloride, glycidyl methacrylate, glyceryl methacrylate, diacetone acrylamide and isoprenol; and
   the at least one anionic monomer is chosen from the group consisting of acrylic acid, methacrylic acid, itaconic acid, crotonic acid, maleic acid, fumaric acid, acrylamido undecanoic acid, 3-acrylamido 3-methylbutanoic acid, maleic anhydride, vinylsulfonic acid, vinylphosphonic acid, allylsulfonic acid, methallylsulfonic acid, 2-methylidenepropane-1,3-disulfonic acid, 2-sulfoethylmethacrylate, sulfopropylmethacrylate, sulfopropylacrylate, allylphosphonic acid, styrene sulfonic acid, and 2-acrylamido-2-methyl propane disulfonic acid; and water-soluble salts of these monomers.

7. The method according to claim 6, wherein the water-soluble (co)polymer is made from between 1 and 99.9 mol % of nonionic monomer(s) in relation to the total number of monomers and comprises from 0.1 to 99 mol % 2-acrylamido-2-methylpropane sulfonic acid, 50% to 100% of the 2-acrylamido-2-methylpropane sulfonic acid being in hydrated crystalline form.

8. The method according to claim 1, wherein the 2-acrylamido-2-methylpropane sulfonic acid in hydrated crystalline form is partially or totally salified before polymerization.

9. The method according to claim 1, wherein the water-soluble (co)polymer is made from the hydrated crystalline form of 2-acrylamido-2-methylpropane sulfonic acid or of at least one of the salts thereof, and from at least one nonionic monomer, and/or at least one anionic monomer.

10. The method according to claim 9, wherein the at least one nonionic monomer is chosen from the group consisting of acrylamide, methacrylamide, N-isopropylacrylamide, N,N-dimethylacrylamide, N,N-diethylacrylamide and N-methylolacrylamide, N-vinylformamide, N-vinyl acetamide, N-vinylpyridine, N-vinylpyrrolidone, N-vinyl imidazole, N-vinyl succinimide, acryloyl morpholine (ACMO), acryloyl chloride, glycidyl methacrylate, glyceryl methacrylate, diacetone acrylamide and isoprenol.

11. The method according to claim 9, wherein the anionic monomer is chosen from acrylic acid, methacrylic acid, itaconic acid, crotonic acid, maleic acid, fumaric acid, acrylamido undecanoic acid, 3-acrylamido 3-methylbutanoic acid, maleic anhydride, vinylsulfonic acid, vinylphosphonic acid, allylsulfonic acid, methallylsulfonic acid, 2-methylidenepropane-1,3-disulfonic acid, 2-sulfoethylmethacrylate, sulfopropylmethacrylate, sulfopropylacrylate, allylphosphonic acid, styrene sulfonic acid, and 2-acrylamido-2-methyl propane disulfonic acid; and water-soluble salts of these monomers.

12. The method according to claim 1, wherein the water-soluble (co)polymer is made from between 1 and 99.9 mol % of nonionic monomer(s) in relation to the total number of monomers and comprises from 0.1 to 99 mol % 2-acrylamido-2-methylpropane sulfonic acid, 50% to 100% of the 2-acrylamido-2-methylpropane sulfonic acid being in hydrated crystalline form.

13. The method according to claim 1, wherein the water-soluble (co)polymer is an anionic (co)polymer based on acrylamide and 2-acrylamido-2-methylpropane sulfonic acid, 50% to 100% of the 2-acrylamido-2-methylpropane sulfonic acid being in the hydrated crystalline form and/or the salts thereof, or a terpolymer of acrylamide, of acrylic acid and of 2-acrylamido-2-methylpropane sulfonic acid, 50% to 100% of the 2-acrylamido-2-methylpropane sulfonic acid being in the hydrated crystalline form and/or the salts thereof.

14. The method according to claim 1, wherein the water-soluble (co)polymer is made from a quantity of anionic monomers of between 5 and 70 mol %.

15. The method according to claim 1, wherein the water-soluble (co)polymer has an average molecular weight in weight of between 0.5 and 40 million g/mol.

16. The method according to claim 1, wherein the quantity of water-soluble (co)polymer added to the aqueous suspension is between 50 and 5,000 g per metric ton of dry solids of suspension.

17. The method according to claim 1, wherein the aqueous suspension of solid particles results from ore extraction and consists of a suspension of mineral particles.

18. The method according to claim 1, wherein the suspension of solid particles contains between 5% and 60% by weight of solids.

19. The method according to claim 1, wherein the aqueous suspension is transported by means of a pipe to a depositing area and wherein the water-soluble (co)polymer is added within said pipe.

20. A method for the flocculation of a suspension of solid particles in water, comprising placing said suspension in contact with at least one water-soluble (co)polymer made from a hydrated crystalline form of 2-acrylamido-2-methylpropane sulfonic acid or of at least one of the salts thereof, the hydrated crystalline form of 2-acrylamido-2-methylpropane sulfonic acid having a 2-theta powder X-ray diffraction diagram comprising peaks at 10.58°, 11.2°, 12.65°, 13.66°, 16.28°, 18.45°, 20°, 20.4°, 22.5°, 25.5°, 25.88°, 26.47°, 28.52°, 30.28°, 30.8°, 34.09°, 38.19°, 40.69°, 41.82°, 43.74°, and 46.04°, all peak values being +/−0.1°.

* * * * *